US009586901B2

(12) United States Patent
Kumar et al.

(10) Patent No.: US 9,586,901 B2
(45) Date of Patent: Mar. 7, 2017

(54) LACTAMS

(75) Inventors: Naresh Kumar, Maroubra (AU); George Iskander, Oakhurst (AU)

(73) Assignee: UNILEVER PLC, London (GB)

( * ) Notice: Subject to any disclaimer, the term of this patent is extended or adjusted under 35 U.S.C. 154(b) by 770 days.

(21) Appl. No.: 12/087,862

(22) PCT Filed: Jan. 24, 2007

(86) PCT No.: PCT/AU2007/000060
§ 371 (c)(1),
(2), (4) Date: Jun. 15, 2012

(87) PCT Pub. No.: WO2007/085042
PCT Pub. Date: Aug. 2, 2007

(65) Prior Publication Data
US 2013/0190377 A1    Jul. 25, 2013

(30) Foreign Application Priority Data

Jan. 24, 2006 (AU) ................................ 2006900343

(51) Int. Cl.

| C07D 207/38 | (2006.01) |
| C08F 26/06 | (2006.01) |
| A01N 43/36 | (2006.01) |
| C07D 207/273 | (2006.01) |
| C07D 207/27 | (2006.01) |
| C07D 207/36 | (2006.01) |
| C07D 207/44 | (2006.01) |

(52) U.S. Cl.
CPC ........... *C07D 207/38* (2013.01); *A01N 43/36* (2013.01); *C07D 207/27* (2013.01); *C07D 207/273* (2013.01); *C07D 207/36* (2013.01); *C07D 207/44* (2013.01); *C08F 26/06* (2013.01)

(58) Field of Classification Search
None
See application file for complete search history.

(56) References Cited

FOREIGN PATENT DOCUMENTS

| WO | 2004/016588 | 2/2004 |
| WO | WO 2004/016588 A1 | 2/2004 |
| WO | WO 2004016588 A1 * | 2/2004 |
| WO | 2005/049600 | 6/2005 |
| WO | WO 2005/049600 A1 | 6/2005 |

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*

(Continued)

*Primary Examiner* — San-Ming Hui
*Assistant Examiner* — Andrew Lee
(74) *Attorney, Agent, or Firm* — Nixon & Vanderhye P.C.

(57) ABSTRACT

Lactams of formulae (I) and (II) and their use in the treatment of microbial infections and microbial contamination of surfaces, particularly infections and surface contaminations characterized by biofilm formation. Compounds of formula (I) and (II) substituted with acrylate or methacrylate groups and their attachment to surfaces or polymers to inhibit microbial contamination are also provided.

34 Claims, 1 Drawing Sheet

(56) References Cited

OTHER PUBLICATIONS

Petrov, V., et al; "Some transformations of 2-acetamido-3-hydroxy-4'-nitropropiophenone"; *Journal of the Chemical Society*, pp. 4066-4075 (1953). Abstract (CAS RN 860361-62-2).
STN File CA, Abstract 145: Poschenrieder, H. et al., Helvetica Chimica ACTA, vol. 89, No. 5, pp. 971-982, (2006).
STN File CA, Abstract 145: Boiadjiev, S.E. et al., Tetrahedron, vol. 62, No. 29, pp. 7043-7055, (2006).
STN File CA, Abstract 140: Cherry, K. et al., Tetrahedron Letters, vol. 45, No. 10, pp. 2063-2066, (2004).
STN File CA, Abstract 140: Quai, M. et al., Tetrahedron Letters, vol. 45, No. 7, pp. 1413-1416, (2004).
STN File CA, Abstract 140: Donnecke, D. et al., Tetrahedron, vol. 59, No. 43, pp. 8499-8507, (2003).
STN File CA, Abstract 137: Ma, S. et al., Journal of Organic Chemistry, vol. 67, No. 18, pp. 6575-6578, (2002).
STN File CA, Abstract 137, Brower, J.O. et al., D.A. Monatshefte Fuer Chemie, vol. 132, No. 12, pp. 1527-1546, (2001).
STN File CA, Abstract 135, Brower, J.O. et al., Tetrahedron, vol. 57, No. 37, pp. 7813-7827, (2001).
STN File CA, Abstract 133, Rosas, N. et al., Journal of Molecular Catalysis A: Chemical, vol. 156, Nos. 1-2, pp. 103-112, (2000).
STN File CA, Abstract 132, Jayasundera, K.P. et al., Bulletin of the Chemical Society of Japan, vol. 73, No. 2, pp. 497-505, (2000).
STN File CA, Abstract 130, Kakiuchi T. et al., Chemistry Letters, No. 10, pp. 1001-1002, (1998).
STN File CA, Abstract 129, Masukawa, T. et al., Chemistry Letters, No. 5, pp. 455-456, (1998).
STN File CA, Abstract 122, Ngwe, H. et al., Bulletin of the Chemical Society of Japan, vol. 67, No. 12, pp. 3320-3326, (1994).
STN File CA, Abstract 120, Kinoshita, H. et al., Chemistry Letters, No. 8, pp. 1441-1442, (1993).
STN File CA, Abstract 109, Adembri, G. et al., Journal of Heterocyclic Chemistry, vol. 25, No. 3, pp. 1019-1022, (1988).
STN File CA, Abstract 107, Coppe-Motte, G. et al., Nato ASI Series C: Mathematical and Physical Sciences, vol. 189, pp. 371-374, (1986).
STN File CA, Abstract 106, Stachel, H.D. et al., Zeitschrift Fuer Naturforschung, Teil B: Anorganische Chemie, Organische Chemie, vol. 41B, No. 5, pp. 640-644, (1986).
STN File CA, Abstract 99, Anselmi, C. et al., Journal of Heterocyclic Chemistry, vol. 20, No. 3, pp. 687-689, (1983).
STN File CA, Abstract 98, Tchissambou, L. et al., Tetrahedron, vol. 38, No. 17, pp. 2687-2695, (1982).
STN File CA, Abstract 93, Engel, J. et al., Chemiker-Zeitung, vol. 103, No. 11, pp. 367-371, (1979).
STN File CA, Abstract 91, Gossauer, A. et al., Chemische Berichte, vol. 112, No. 6, pp. 2243-2255, (1979).
STN File CA, Abstract 49, Petrov, V et al., Journal of the Chemical Society, pp. 4066-4075, (1953).
STN File CA, Abstract 44, Brown, E.V. et al., Chemistry of Penicillin, pp. 473-534, (1949).
PCT International Preliminary Report on Patentability; Int'l Application No. PCT/AU2007/00060; Int'l Filing Date Jan. 24, 2007 (7 pgs).
Poschenrieder, H., et al; *Helvetica Chimica ACTA* (2006), 89(5), pp. 971-982, Abstract.
Boiadjiev, S.E., et al; *Tetrahedron* (2006), 69(29), pp. 7043-7055, Abstract.
Cherry, K., et al; *Tetrhedron Letters* (2004), 45(10), pp. 2063-2066 Abstract.
Quai, M., et al; *Tetrahedron Letters* (2004), 45(7), pp. 1413-1416, Abstract.
Donnecke, D. et al; *Tetrahedron* (2003), 59(43), pp. 8499-8507, Abstract.
Ma, S., et al; *Journal of Organic Chemistry* (2002), 67(18), pp. 6575-6578, Abstract.
Brower, J.O., et al; *Monatshefte fuer Chemie* (2001), 132(12), pp. 1527-1546, Abstract.
Brower, J.O., et al; *Tetrahedron* (2001), 57(37), pp. 7813-7827, Abstract.
Rosas, N., et al; *Journal of Molecular Catalysis A: Chemical* (2000), 156(1-2), pp. 103-112, Abstract.
Jayasundera, K.P., et al; *Bulletin of the Chemical Society of Japan* (2000), 73(2), pp. 497-505, Abstract.
Kakiuchi, T., et al; *Chemistry Letters* (1998), 10, pp. 1001-1002, Abstract.
Masukawa, T., et al; *Chemistry Letters* (1998), 5, pp. 455-456, Abstract.
Ngwe, H., et al; *Bulletin of the Chemical Society of Japan* (1994), 67(12), pp. 3320-3326, Abstract.
Kinoshita, H., et al; *Chemistry Letters* (1993), 8, pp. 1441-1442, Abstract.
Adembri, G., et al; *Journal of Heterocyclic Chemistry* (1988), 25(3), pp. 1019-1022, Abstract.
Coppe-Motte, G., et al; *Nato ASI Series C: Mathematical and Physical Sciences* (1986), 189, pp. 371-374, Abstract.
Stachel, H.D., et al; *Zeitschrift fuer Naturforschung, Teil B: Anorganische Chemie, Organsiche Chemie* (1986), 41B(5), pp. 640-644, Abstract.
Anselmi, C., et al; *Journal of Heterocyclic Chemistry* (1983), 20(3), pp. 687-689, Abstract.
Tchissambou, L., et al; *Tetrahedron* (1982), 38(17), pp. 2687-2695, Abstract.
Engel, J., et al; *Chemiker-Zeitung* (1979), 103(11), pp. 367-371, Abstract.
Gossauer, A, et al; *Chemische Berichte* (1979), 112(6), pp. 2243-2255, Abstract.
Petrov, V., et al; *Journal of the Chemical Society* (1953) pp. 4066-4075, Abstract.
Brown, E.V., et al; *Chemistry of Penicillin* (1949), pp. 473-534, Abstract.

\* cited by examiner

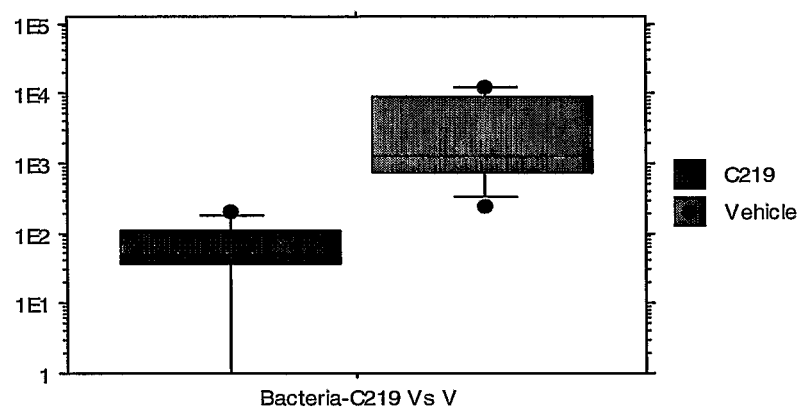

LACTAMS

This application is the U.S. national phase of International Application No. PCT/AU2007/000060 filed 24 Jan. 2007 which designated the U.S. and claims priority to 2006900343 filed 24 Jan. 2006, the entire contents of each of which are hereby incorporated by reference.

FIELD OF THE INVENTION

The present invention relates to novel lactams, methods for their synthesis and uses of these compounds.

BACKGROUND OF THE INVENTION

In International Patent Application No. WO 2004/016588 (the disclosure of which is hereby incorporated by reference), the present applicant disclosed a method of synthesising lactams of formulae A and B by reacting an appropriate 5-halomethylene substituted furanone with an amine under mild conditions to give lactams of general formula A, optionally followed by dehydration to give lactams of general formula B.

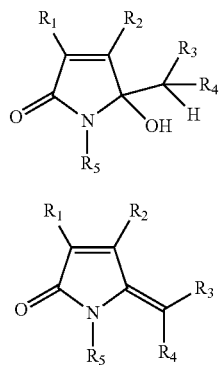

Each of the lactams exemplified in the specification of WO 2004/016588 included one or more bromine substituents, usually at position $R_3$ or $R_4$. Positions $R_1$ and $R_2$ were substituted with halo, alkyl (substituted or unsubstituted) or hydrogen. The lactams were shown to have antibacterial properties and to act as quorum sensing inhibitors.

SUMMARY OF THE INVENTION

The present invention is directed to members of a novel class of lactams comprising a heterocyclyl, heteroaryl, aryl or arylalkyl substituent at the 3 or 4 position of the lactam ring and which are not brominated on the exocyclic methylene group. The lack of bromination on the exocyclic methylene group improves the stability of these compounds relative to the compounds exemplified in WO 2004/016588. In addition, the presence of a heteroaryl, aryl or arylaklyl substituent at the 3 or 4 position provides additional in vivo stability when compared to the compounds exemplified in WO 2004/016588 that bear an alkyl group. The compounds have been shown to have antibacterial properties. Further, at least some of the compounds of the present invention have surprisingly improved antibacterial activity and/or surprisingly reduced cytotoxicity when compared to the certain lactams exemplified in the specification of WO 2004/016588. The present inventors have also found that analogues of these compounds can be substituted with acrylate and methacrylate groups so that these compounds can be readily polymerised, copolymerised or attached to surfaces which bear functional groups by, for example, the Michael addition reaction.

Accordingly, in a first aspect, the present invention provides a compound of formula I:

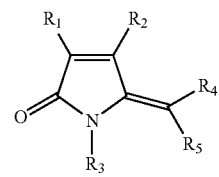

wherein:

$R_1$ and $R_2$ are each independently selected from the group consisting of hydrogen, halogen, alkyl, cycloalkyl, alkoxy, oxoalkyl, alkenyl, heterocyclyl, heteroaryl, aryl, and arylalkyl;

$R_3$ is selected from the group consisting of hydrogen, hydroxy, alkyl, cycloalkyl, alkoxy, oxoalkyl, alkenyl, heterocyclyl, heteroaryl, cycloalkyl, aryl, arylalky, and —C(O)CR_6=CH_2;

$R_4$ and $R_5$ are each selected from the group consisting of hydrogen, aryl, heterocyclyl, heteroaryl, and arylalkyl provided that at least one of $R_4$ and $R_5$ is hydrogen;

$R_6$ is selected from the group consisting of hydrogen or methyl;

with the proviso that at least one of $R_1$ and $R_2$ is selected from the group consisting of heterocyclyl, heteroaryl, aryl and arylalkyl.

In a second aspect, the present invention provides a compound of formula (II):

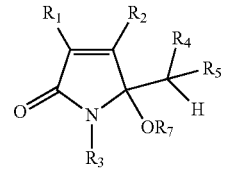

wherein $R_1$ and $R_2$ are each independently selected from the group consisting of hydrogen, halogen, alkyl, cycloalkyl, alkoxy, oxoalkyl, alkenyl, heterocyclyl, heteroaryl, aryl, and arylalkyl;

$R_3$ is selected from the group consisting of hydrogen, hydroxy, alkyl, cycloalkyl, alkoxy, oxoalkyl, alkenyl, heterocyclyl, heteroaryl, aryl, arylalkyl, and —C(O)CR_6=CH_2;

$R_4$ is selected from the group consisting of hydrogen, aryl, heterocyclyl, heteroaryl and arylalkyl;

$R_6$ is selected from the group consisting of hydrogen or methyl;

$R_7$ is selected from the group consisting of H and —C(O)CR_6=CH_2;

with the proviso that at least one of $R_1$ and $R_2$ is selected from the group consisting of heterocyclyl, heteroaryl, aryl and arylalkyl.

In a third aspect, the present invention provides a method of treating or preventing a microbial infection of a subject, the method comprising administering a compound of Formula I or a compound of Formula II to the subject.

In a fourth aspect, the present invention provides a method of inhibiting or preventing microbial contamination of a surface, the method comprising administering the compound of Formula I or a compound of Formula II to the surface.

In a fifth aspect, the present invention provides a pharmaceutical formulation comprising a compound of Formula I or a compound of Formula II and a carrier.

In a sixth aspect, the present invention provides a compound of Formula I wherein $R_3$ is —C(O)CR$_6$=CH$_2$.

In a seventh aspect, the present invention provides a compound of Formula II wherein at least one of $R_3$ and $R_7$ is selected from —C(O)CR$_6$=CH$_2$.

Preferably, each of $R_3$ and $R_7$ is selected from —C(O)CR$_6$=CH$_2$.

In an eighth aspect, the present invention provides a compound according to the sixth or seventh aspect when used to form an oligomer or polymer In a ninth aspect, the present invention provides a polymer or oligomer formed by oligomerising or polymerising a compound according to the sixth or seventh aspect directly or with one or more other monomers.

In a tenth aspect, the present invention provides a compound of the sixth or seventh aspect when the terminal vinyl group of the compound is reacted with a functional group.

In an eleventh aspect, there is provided a compound according to the sixth or seventh aspect when attached to a surface.

In a twelfth aspect, there is provided a surface comprising one or more compounds of the sixth or seventh aspect attached to the surface.

BRIEF DESCRIPTION OF THE FIGURES

FIG. 1. shows the lung bacterial loads between two groups of mice after challenge with *Pseudomonas aeruginosa* PAO1 (wt) $5.2\times10^6$ CFU/lung ($1.3\times10^8$ CFU/ml) at day 5. The first group was treated with 5-methylene-4-phenyl-dihydro-pyrrol-2-one (C219) as 12 μg/g body weight, given as injections twice a day for three days and the second group were treated with vehicle. (p=0.0008).

DETAILED DESCRIPTION OF THE INVENTION

In a first aspect, the present invention provides a compound of formula I:

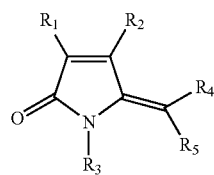

I wherein:

$R_1$ and $R_2$ are each independently selected from the group consisting of hydrogen, halogen, alkyl, cycloalkyl, alkoxy, oxoalkyl, alkenyl, heterocyclyl, heteroaryl, aryl, and arylalkyl;

$R_3$ is selected from the group consisting of hydrogen, hydroxy, alkyl, cycloalkyl, alkoxy, oxoalkyl, alkenyl, heterocyclyl, heteroaryl, cycloalkyl, aryl, arylalky, and —C(O)CR$_6$=CH$_2$;

$R_4$ and $R_5$ are each selected from the group consisting of hydrogen, aryl, heterocyclyl, heteroaryl, and arylalkyl provided that at least one of $R_4$ and $R_5$ is hydrogen;

$R_6$ is selected from the group consisting of hydrogen or methyl;

with the proviso that at least one of $R_1$ and $R_2$ is selected from the group consisting of heterocyclyl, heteroaryl, aryl and arylalkyl.

The present invention also provides for the starting materials used in the preparation of the compounds of Formula I. These starting materials have been found to have antibacterial activity in their own right.

Accordingly, in a second aspect, the present invention provides a compound of formula II:

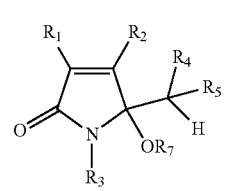

II wherein $R_1$ and $R_2$ are each independently selected from the group consisting of hydrogen, halogen, alkyl, cycloalkyl, alkoxy, oxoalkyl, alkenyl, heterocyclyl, heteroaryl, aryl, and arylalkyl;

$R_3$ is selected from the group consisting of hydrogen, hydroxy, alkyl, cycloalkyl, alkoxy, oxoalkyl, alkenyl, heterocyclyl, heteroaryl, aryl, arylalkyl, and —C(O)CR$_6$=CH$_2$;

$R_4$ is selected from the group consisting of hydrogen, aryl, heterocyclyl, heteroaryl and arylalkyl;

$R_6$ is selected from the group consisting of hydrogen or methyl;

$R_7$ is selected from the group consisting of H and —C(O)CR$_6$=CH$_2$;

with the proviso that at least one of $R_1$ and $R_2$ is selected from the group consisting of heterocyclyl, heteroaryl, aryl and arylalkyl.

Preferably, each of $R_4$ and $R_5$ is hydrogen.

Preferably, $R_2$ is selected from the group consisting of heterocyclyl, heteroaryl, aryl and arylalkyl.

In a preferred form, the compound is selected from the group consisting of the following compounds set out in the examples: 5-methylene-4-phenyl-dihydro-pyrrol-2-one, 1-methyl-5-methylene-4-phenyl-dihydro-pyrrol-2-one, 5-methylene-1,4-diphenyl-dihydro-pyrrol-2-one, 4-(4'-bromophenyl)-5-methylene-2-dihydro-pyrrol-2-one, 4-benzyl-5-methylene-dihydro-pyrrol-2-one, 4-(4'-methoxyphenyl)-5-methylene-dihydro-pyrrol-2-one, 5-methylene-4-(4'-fluorophenyl)-dihydro-pyrrol-2-one, 5-methylene-4-(4'-trifluoromethylphenyl)-dihydro-pyrrol-2-one, 5-methylene-4-(3'-trifluoromethylphenyl)-dihydro-pyrrol-2-one, 5-methylene-4-(2'-fluorophenyl)-dihydro-pyrrol-2-one and 5-methylene-4-(3'-fluorophenyl)-dihydro-pyrrol-2-one.

In a third aspect, the present invention provides a method of treating a microbial infection in a subject, the method comprising administering a compound of Formula I or Formula II to the subject.

The microbial infection may be a bacterial, protozoal or fungal infection. Preferably, the infection is a bacterial infection.

Suitable methods of administration are disclosed in WO 2004/016588, the disclosure of which is hereby incorporated by reference. Examples of the types of bacterial infections that may be treated by the methods of the present invention are also disclosed in WO 2004/016588.

The compounds of the present invention can act as quorum sensing inhibitors. The compounds therefore find use in any application where the inhibition of quorum sensing is desired. For example, the compounds of the present invention may have use in preventing the establishment of biofilms and expression of virulence by microorganisms through the inhibition of quorum sensing systems and/or other extracellular systems (eg see, WO 01/47681, the disclosure of which is incorporated herein in its entirety).

Quorum sensing pathways (such as those involving homoserine lactones) are present in a wide range of bacteria. The formation of biofilms is one instance of quorum sensing.

The following is a non-exhaustive list of groups of Gram-Negative bacteria that have members which use homoserine lactones for cell-cell communication: anaerobic Gram Negative Straight, Curved and Helical Rods; Bacteroidaceae; The Rickettsias and Chlamydias; Dissimilatory Sulfate- or Sulfur-Reducing Bacteria; the Mycoplasmas; The Mycobacteria; Budding and/or Appendaged Bacteria; Sheathed Bacteria; Nocardioforms; and Actinomycetes, for example. See Bergey's Manual of Systematic Bacteriology, First Ed., John G. Holt, Editor in Chief (1984), incorporated herein by reference.

Further microbial infections that may be treated by the compounds of the present invention include bacterial infections caused by *Staph. aureus, Staph epidermis, Serratia* spp., *Vibrio* spp., and *Strep. pneumonia*; protozoal infections caused by *Acanthamoeba*; and fungal infections caused by *Fusarium* spp.

Preferably, the method of the third aspect may be used to treat or prevent a microbial infection in a subject that is characterised by biofilm formation.

The present invention is suitable for biofilms originating from a single type of organism and for mixed biofilms. By "mixed biofilms" is meant biofilms created by more than one type of microorganism. It is envisioned that mixed biofilms could be created by at least two organisms from the group consisting of bacteria, algae, fungi, and protozoa.

Non-limiting examples of human infections involving biofilms include dental caries, periodontitis, otitis media, muscular skeletal infections, necrotising fascitis, biliary tract infection, osteomyelitis, bacterial prostatitis, native valve endocarditis, cystic fibrosis pneumonia, meloidosis, and nosocomial infections such as ICU pneumonia, urinary catheter cystitis, peritoneal dialysis (CAPD) peritonitis, and biliary stent blockage. Biofilm formation can affect sutures, exit sites, arteriovenous sites, scleral buckles, contact lenses, IUDs, endotracheal tubes, Hickman catheters, central venous catheters, mechanical heart valves, vascular grafts, orthopedic devices, penile prostheses. Further applications are described in Costerton J et al, (1999) Vol. 284, Science pp 1318-1322 and Costerton J and Steward, (2001) Battling Biofilms, Scientific American pp 75-81, the disclosures of which are incorporated herein by reference.

Other locations in which biofilms may form include dental plaque which may lead to gum disease and cavities, contact lenses which may lead to eye infections, ears which may lead to chronic infection and lungs which may lead to pneumonia.

The infection may be cystic fibrosis. The infection may be that resulting from a skin infection, burn infection and/or wound infection. The method and composition of the invention may be particularly suitable for the treatment of infection in immuno compromised individuals.

The compounds of the present invention have been shown to be particularly effective in preventing microbial contamination of surfaces, in particularly by preventing the formation of biofilms.

Accordingly, in a fourth aspect, the present invention provides a method of inhibiting microbial contamination of a surface, the method comprising administering a compound of Formula I or Formula II to the surface.

The microbial contamination may be protozoal, fungal or bacterial contamination.

In a preferred form, the microbial contamination is a bacterial contamination. In a more preferred form, the bacterial contamination is a biofilm.

The surface may be any natural or artificial surface. By "artificial surface", is meant any surface that is not naturally occurring. In one embodiment, the surface is not an external surface (eg skin) or an internal surface of a human being or animal. In another embodiment, the surface is an external surface or an internal surface of a human being or animal. Examples of surfaces that might be treated using the compounds of Formula I or Formula II are disclosed in WO 2004/016588.

The compound may be administered by any suitable means. For instance, the compound may be attached to the surface using the techniques and surfaces described in WO 2004/016588. Suitable surfaces include the surfaces of articles for which it is desirable to prevent bacterial contamination. These include: medical devices, for example, implantable biomedical devices such as urinary catheters, percutaneous access catheters, stents, orthopaedic implants, bone and dental ceramics and polymers as well as non-implantable devices such as contact lenses, contact lens storage cases, and the like.

Other suitable surfaces include the interiors of pipes and vessels used to distribute oil and gas. The interior surfaces of oil pipelines can be readily contaminated by biofilms which impede the flow of oil in the pipeline and hence its efficiency.

The material from which the article is formed can be a metal, a ceramic, a solid synthetic polymer, or a solid natural polymer, for example a solid biopolymer. Examples of useful materials for this invention are titanium, hydroxyapatite, polyethylene (which are useful materials for orthopaedic implants), polyurethanes, organosiloxane polymers, perfluorinated polymers (which are useful materials for instance for catheters, soft tissue augmentation, and blood contacting devices such as heart valves), acrylic hydrogel polymers, HEMA/GMA polymers and silicon/siloxane hydrogel polymers (for instance for contact lens and intraocular lens applications), and the like, and any combination thereof. Further included are resin composites, components and resin-modified glass ionomers used in oral care. The surfaces of these materials can be chemically inert or contain reactive functional groups.

Further examples of articles include archival documents, antiques and art, rare and valuable seeds intended for storage (e.g. seed banks of conservation groups), etc in which case the substrate may be paper, material or other natural or synthetic material.

The article may be a shell fish or aquaculture apparatus, for example, that described in WO 99/05227, the disclosure of which is incorporated herein by reference.

The surface of the article may be any hard surface such as metal, organic and inorganic polymer surface, natural and synthetic elastomers, board, glass, wood, paper, concrete, rock, marble, gypsum and ceramic materials which optionally are coated, eg with paint, enamel etc; or any soft surface such as fibres of any kind (yams, textiles, vegetable fibres, rock wool, hair etc.); or porous surfaces; skin (human or animal); keratinous materials (nails etc.). The hard surface can be present in process equipment or components of cooling equipment, for example, a cooling tower, a water treatment plant, a dairy, a food processing plant, a chemical or pharmaceutical process plant. The porous surface can be present in a filter, eg. a membrane filter.

Particular examples of articles whose surfaces may be treated in accordance with the invention include, but are not limited to, toilet bowls, bathtubs, drains, highchairs, counter tops, vegetables, meat processing rooms, butcher shops, food preparation areas, air ducts, air-conditioners, carpets, paper or woven product treatment, nappies (diapers), personal hygiene products (eg sanitary napkins) and washing machines. The compounds may be formulated in the form of a toilet drop-in or spray-on devices for prevention and removal of soil and under rim cleaner for toilets. The compounds of the present invention also have applications in cleaning of Industrial surfaces such as floors, benches, walls and the like and these and other surfaces in medical establishments such as hospitals (eg surfaces in operating theatres), veterinary hospitals, and in mortuaries and funeral parlours.

Further examples of surfaces which may be treated include hard, rigid surfaces such as drain pipes, glazed ceramic, porcelain, glass, metal, wood, chrome, plastic, vinyl and formica or soft flexible surfaces such as shower curtains, upholstery, laundry and carpeting. It is also envisioned that both woven and non woven and porous and non-porous surfaces would be suitable.

The compound may be administered by any suitable means. For instance, the compound may be attached to the surface using the techniques and surfaces described in WO 2004/016588. Examples include providing the compounds of the present invention as part of an oligomer or polymer by, for instance, co-polymerising the compound with other monomers or attaching the compound to the polymer backbone by techniques well known to those in the art.

Methods for the covalent immobilization of organic molecules onto solid surfaces are well known to those skilled in the art. Interfacial reactions leading to the formation of covalent interfacial bonds are derived from well known organic-synthetic reactions. The choice of immobilization reaction depends on both the nature of the substrate material and the chemical composition of the compound of the present invention that is desired for a particular application.

For example, a compound that contains a hydroxyl group in a side chain distal to the ring system, can be linked covalently onto surfaces using epoxide chemistry analogous to the reaction pathway described for the immobilization of polysaccharides onto epoxidated surfaces in Li et al., Surface Modification of Polymeric Biomaterials (B D Ratner and D G Castner, Eds), Plenum Press, NY, 1996 pages 165-173 (the disclosure of which is incorporated herein in its entirety), through isocyanate groups attached to the surface to produce stable urethane linkages through thermal processes, or through carboxylic acid groups or their equivalents, such as acid chlorides, on the surface to produce ester linkages. A compound that contains an aldehyde group can be linked onto surface amine groups using a reductive animation reaction. A compound that contains a carboxylic acid group can be linked onto surface amine groups using carbodiimide chemistry.

Interfacial coupling reactions must of course be selected not only for their ability to achieve the desired covalent linkage but also for avoidance of adverse effects on the furanone compound (s) to be attached. Particularly, the furanone ring system tends to be labile to alkaline conditions. Such limitations are well known to those skilled in the art. Among the many possible interfacial coupling reactions known in the art, there is sufficient scope for selection of reactions that proceed in a suitable pH range and with furanones substituted with various functional groups in various positions.

Some solid substrate materials possess reactive surface chemical groups that can undergo chemical reactions with a partner group on a compound and thereby form a covalent interfacial linkage directly.

Alternatively, in situ covalent linkage can be made directly through the addition of a doubly functionalised linker molecule to the active surface in the presence of an appropriate compound, or stepwise by sequential addition of doubly functionalised linker molecules and then an appropriate compound. It is not always possible to immobilize furanone compounds directly onto solid substrate materials; in these cases, surface activation or one or more interfacial bonding layer (s) is used to effect covalent immobilization of the compounds.

Surface activation of solid substrate materials can be achieved in a number of ways. Examples are corona discharge treatment or low pressure plasma treatment of polymers. These methods are well known to introduce a variety of functional groups onto polymeric surfaces.

An alternative approach is to provide an interfacial bonding layer interspersed between the solid substrate material or medical device and the compound layer. The application of a thin interfacial bonding layer can be done using methods such as dip coating, spin coating, or plasma polymerization. The chemistry of the bonding layer is selected such that appropriate reactive chemical groups are provided on the surface of this layer, groups that then are accessible for reaction with compound of the invention.

Particularly versatile is the subsequent application of multiple thin interfacial bonding layers; this method can provide a very wide range of desired chemical groups on the surface for the immobilization of a wide range of functionalized furanones and enables usage of compounds optimized for their biological efficacy.

By providing a thin, surface-coated layer of compounds, the optical quality of antibacterial devices of this invention is not reduced, which makes the invention applicable to transparent ophthalmic devices such as contact lenses and intraocular lenses.

The present invention provides thin surface coatings that provide antimicrobial properties and/or antifungal properties to solid materials onto which the coatings have been applied. More particularly, the coatings may be designed to reduce or prevent colonization of biomedical devices by bacteria that cause adverse effects on the health of human users of biomedical devices when such devices are colonized by bacteria.

Alternatively, the compound may be administered in the form of a formulation.

Accordingly, in a fifth aspect, the present invention provides a formulation comprising a compound of Formula I or Formula II and a carrier.

Examples of the types of carrier that may be used with the compounds of Formula I or Formula II are disclosed in WO 2004/016588.

The formulations may be in any suitable form. The formulation may include a carrier or diluent. The carrier may be liquid or solid. For example, the compositions may be in the form of a solution or suspension of at least one of the compounds in a liquid. The liquid may be an aqueous solvent or a non-aqueous solvent. The liquid may consist of or comprise a one or more organic solvents. The liquid may be an ionic liquid. Particular examples of carrier or diluents include, but are not limited to, water, polyethylene glycol, propylene glycol, cyclodextrin and derivatives thereof.

The composition may be formulated for delivery in an aerosol or powder form.

The composition may include organic or inorganic polymeric substances. For example, the compound of the invention may be admixed with a polymer or bound to, or adsorbed on to, a polymer.

When the composition is to be formulated as a disinfectant or cleaning formulation, the composition may include conventional additives used in such formulations. Non-limiting examples of the physical form of the formulations include powders, solutions, suspensions, dispersions, emulsions and gels.

A compound of the invention may be incorporated into epidermal bandages and lotions. Alternatively, the compounds of the invention may be incorporated into cosmetic formulations, for example, aftershave lotions, skin creams, deodorants and anti-dandruff shampoos.

Compositions of the present invention may be in the form of an aqueous solution or suspension containing a cleaning-effective amount of the active compound described above. The cleaning composition may be in the form of a spray, a dispensable liquid, or a toilet tank drop-in, under-rim product for prevention, removal and cleaning of toilets and other wet or intermittently wet surfaces in domestic or industrial environments.

The compositions of the present invention may additionally comprise a surfactant selected from the group consisting of anionic, non-ionic, amphoteric, biological surfactants and mixtures thereof. Most preferably, the surfactant is sodium dodecyl sulfate.

One or more adjuvant compounds may be added to the cleaning solution of the present invention. They may be selected from one or more of biocides, fungicides, antibiotics, and mixtures thereof to affect planktonics. pH regulators, perfumes, dyes or colorants may also be added. In addition, the adjuvant could be a cell permeabilisation agent such as EDTA or FDS.

In a preferred from, "cleaning-effective amount of active compound" means the amount of the compound required to remove at least 10% of bacteria from a biofilm as determined by a reduction in numbers of bacteria within the biofilm when compared with a biofilm not exposed to the active compound.

Preferably, the formulation is a pharmaceutical formulation.

Formulations for pharmaceutical uses may incorporate pharmaceutically acceptable carriers, diluents and excipients known to those skilled in the art. The formulations make be formulated for parenteral or non-parenteral administration. The formulations may be formulated for methods of introduction including, but not limited to, topical, intradermal, intramuscular, intraperitoneal, intravenous, subcutaneous, intranasal, epidural, ophthalmic, and oral routes. They may be formulated for administration by any convenient route, for example by infusion or bolus injection, by absorption through epithelial or mucocutaneous linings (e.g., oral mucosa, rectal and intestinal mucosa, etc.) and may be administered together with other biologically active agents. Administration may be localized or systemic. The formulation may be formulated for intraventricular and intrathecal injection.

Pulmonary administration can also be employed, e.g., by use of an inhaler or nebulizer, and formulation with an aerosolizing agent.

In certain preferred embodiments the formulation further comprises other active agents such as antibiotics and cleaning agents.

In other embodiments of the present invention, the formulation may be formulated as a dentifrice, a mouthwash or a composition for the treatment of dental caries. The composition may be formulated for acne treatment or cleaning and disinfecting contact lenses (eg as a saline solution).

The present inventors have also devised methods of preparing analogues of the compounds of Formula I and Formula II which are functionalised with a vinyl group. The vinyl group allows the functionalised compounds to be readily incorporated in polymers and/or attached to surfaces.

Accordingly, in a sixth aspect, the present invention provides a compound of Formula I wherein $R_3$ is —C(O)CR$_6$=CH$_2$.

Further, in a seventh aspect, the present invention provides a compound of Formula II wherein at least one of $R_3$ and $R_7$ is selected from —C(O)CR$_6$=CH$_2$.

In an eighth aspect, the present invention provides a compound of the sixth or seventh aspect when used to form an oligomer or polymer.

Preferably, the oligomer or polymer is formed by polymerisation of the terminal vinyl group of the compound of the sixth or seventh aspect In a ninth aspect, the present invention provides a polymer or oligomer formed by oligomerising or polymerising a compound of the sixth or seventh aspect directly or with one or more other monomers.

The one or more other monomers may be any suitable polymerisable comonomer eg acrylate ester such as alkyl, hydroxyalkyl, aminoalkyl, or substituted aryl, acrylates or methacrylates, crotonates, substituted or unsubstituted acrylonitriles, vinyl alcohols or acteates, and styrenes.

The vinyl group of the compounds of the sixth and seventh aspects allows for polymerisation or reaction with other unsaturated systems. It also allows for reaction with other functional groups by, for example, Michael addition. Other strategies for reacting a vinyl group with a functional group to create a covalent bond are well known to those skilled in the art.

Accordingly, in a tenth aspect, the present invention provides a compound of the sixth or seventh aspects when the terminal vinyl group of the compound is reacted with a functional group.

The functional group may be, for instance, an amine or a thiol group. Preferably, the reaction is with an amine. More preferably, a primary amine.

Surfaces comprising a compound of the sixth or seventh aspect attached thereto would be expected to prevent or inhibit colonisation of the surface by bacteria.

Accordingly, in an eleventh aspect, there is provided a compound of the sixth or seventh aspect when attached to a surface.

As mentioned above, suitable surfaces to which a compound according to the present invention may be attached are detailed in WO 2004/016588. In a preferred form, the surface is the surface of a contact lens.

Preferably, the compound of the sixth or seventh aspect is attached to the surface by reaction of the terminal vinyl group of the compound with a functional group.

More preferably, the functional group is a primary amine.

In a twelfth aspect, there is provided a surface comprising one or more compounds of Formula II attached to the surface.

The term "alkyl" is taken to mean both straight chain and branched alkyl groups such as methyl, ethyl, propyl, isopropyl, butyl, isobutyl, sec-butyl, tertiary butyl, and the like.

Preferably the alkyl group is a lower alkyl of 1 to 10 carbon atoms, more preferably 1 to 6 carbon atoms.

In certain embodiments, the carbon chain of the alkyl group is interrupted with one or more heteroatoms. For instance, a polyethylene glycol group of the form $—(CH_2CH_2O)_nH$ is to be understood to be an alkyl group of such an embodiment.

The term "cycloalkyl" as used herein refers to cyclic hydrocarbon groups. Suitable cycloalkyl groups include but are not limited to cyclopropyl, cyclobutyl and cyclohexyl.

The term "alkoxy" denotes straight chain or branched alkyloxy, preferably $C_{1-10}$-alkoxy. Examples include methoxy, ethoxy, n-propoxy, isopropoxy and the different butoxy isomers.

The term "alkenyl" includes groups formed from straight chain, branched or mono- or polycyclic alkenes and polyenes. Substituents include mono- or poly-unsaturated alkyl or cycloalkyl groups as previously defined, preferably $C_{2-10}$alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, or 1,3,5,7-cyclooctatetraenyl.

The term "alkynyl" as used herein, refers to straight chain or branched hydrocarbon groups containing one or more triple bonds. Suitable alkynyl groups include, but are not limited to ethynyl, propynyl, butynyl, pentynyl and hexenyl.

The term "halogen" includes fluorine, chlorine, bromine or iodine, preferably bromine or fluorine.

The term "heteroatoms" denotes O, N, S or Si.

The term "acyl" used either alone or in compound words such as "acyloxy", "acylthio", "acylamino" or "diacylamino" denotes an alkanoyl, aroyl, heteroyl, carbamoyl, alkoxycarbonyl, alkanesulfonyl, arysulfonyl, and is preferably a $C_{1-10}$ alkanoyl. Examples of acyl include carbamoyl; straight chain or branched alkanoyl, such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl; alkoxycarbonyl, such as methoxycarbonyl, ethoxycarbonyl, t-butoxycarbonyl, t-pentyloxycarbonyl or heptyloxycarbonyl; cycloalkanecarbonyl such as cyclopropanecarbonyl cyclobutanecarbonyl, cyclopentanecarbonyl or cyclohexanecarbonyl; alkanesulfonyl, such as methanesulfonyl or ethanesulfonyl; alkoxysulfonyl, such as methoxysulfonyl or ethoxysulfonyl; heterocycloalkanecarbonyl; heterocyclyoalkanoyl, such as pyrrolidinylacetyl, pyrrolidinylpropanoyl, pyrrolinylacetyl, pyrrolylacetyl, pyrrolidinylbutanoyl, pyrrolidinylpentanoyl, pyrrolidinylhexanoyl or thiazolidinylacetyl; heterocyclylalkenoyl, such as heterocyclylpropenoyl, heterocyclylbutenoyl, heterocyclylpentenoyl or heterocyclylhexenoyl; or heterocyclylglyoxyloyl, such as, thiazolidinylglyoxyloyl or pyrrolidinylglyoxyloyl.

The term "aryl" refers to aryl groups having 6 through 10 carbon atoms and includes, for example, phenyl, naphthyl, indenyl. Preferably, the aryl group is phenyl or naphthyl.

The term "arylalkyl" includes groups such as benzyl and phenethyl groups which comprise an alkyl chain with an aryl substituent.

The term "heterocyclyl" includes monocyclic, polycyclic, fused or conjugated hydrocarbon residues, preferably C3-6, wherein one or more carbon atoms (and where appropriate, hydrogen atoms attached thereto) are replaced by a heteroatom so as to provide a non-aromatic residue. Suitable heteroatoms include O, N, and S. When two or more carbon atoms are replaced, this may be by two or more of the same heteroatom or by different heteroatoms. Suitable examples of heterocyclic groups include pyrollodinyl, piperidyl, piperazinyl, morpholino, quinolinyl, isoquinolinyl, thiomorpholino, dioxanyl, tetrahydrofuranyl, tetrahydropyranyl, and tetrahydropyrrolyl.

The term "heteroaryl" includes a 5- or 6-membered heteroaromatic ring containing one or more heteroatoms selected from O, N and S. Suitable examples of heteroaryl groups include tetrazolyl, 1,2,3-triazolyl, 1,2,4-triazolyl, imiidazolyl, pyrazolyl, pyridinyl, pyrimidinyl, oxazolyl, and oxadiazolyl.

Each alkyl, cycloalkyl, alkoxy, oxoalkyl, alkenyl, heterocyclyl, heteroaryl, aryl, and arylalkyl group may optionally be substituted by one or more groups selected from alkyl, cycloalkyl, alkenyl, alkynyl, aryl, arylalkyl, heterocyclyl, heteroaryl, halo, carboxyl, haloalkyl, haloalkynyl, hydroxy, substituted or unsubstituted alkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocyclyl, heterocycloxy, heterocyclamino, haloheterocyclyl, alkylsulfenyl, alkylcarbonyloxy, alkylthio, acylthio, phosphorus-containing groups such as phosphono and phosphinyl.

In order that the nature of the present invention may be more clearly understood, preferred forms thereof will now be described with reference to the following non-limiting examples.

EXAMPLES

1. Compound Synthesis

General Procedure:

Reaction Scheme:

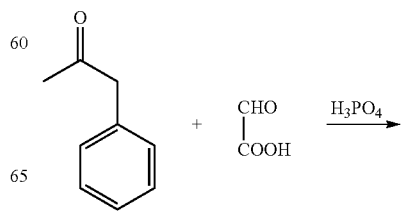

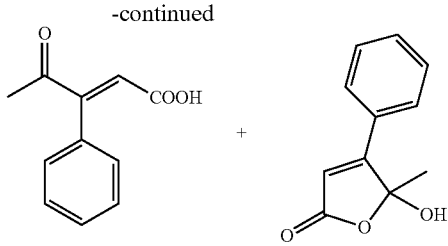

Synthesis of 3-phenyl-4-oxo-2-pentenoic acid

Glyoxilic acid (42.3 g; 0.45 mol), phenyl acetone (40.2 g; 0.3 mol) and phosphoric acid 30 ml; 85%) were heated together at 75-80° C. for 5 hrs, after which the mixture was left standing to cool overnight at room temperature. The dark coloured reaction mixture was poured into brine (100 ml) and extracted with $CH_2Cl_2$:$Et_2O$ (1:1; v/:v) (3×50 ml). The combined extracts was washed with three times with brine, dried ($Na_2SO_4$), and evaporated in vacuo leaving a brown syrupy oil (50 g). The syrup was re-dissolved in dichloromethane (100 ml) and extracted with saturated sodium bicarbonate (3×65 ml). The organic phase was dried ($Na_2SO_4$) and evaporated to yield 5-hydroxy-5-methyl-4-phenyl-2(5H)furanone as a syrupy oil which solidified on keeping (3.3 g; 6%). Colourless crystals from $CH_2Cl_2$/petrol, m.p. 105-107° C.

The combined bicarbonate solution was acidified with 2M hydrochloric acid and extracted with $CH_2Cl_2$ (3×40 ml). The dichloromethane extracts were washed with brine, dried ($Na_2SO_4$) and evaporated to yield 3-phenyl-4-oxo-2-pentenoic acid as a pale yellow oil which solidifies on standing in the fridge (41 g; 72%). Colourless crystals from petrol/$CH_2Cl_2$, m.p. 70° C.

Reaction Scheme:

Scheme 1: Synthesis of 5-methylene-4-phenyl-dihydro-pyrrol-2-one

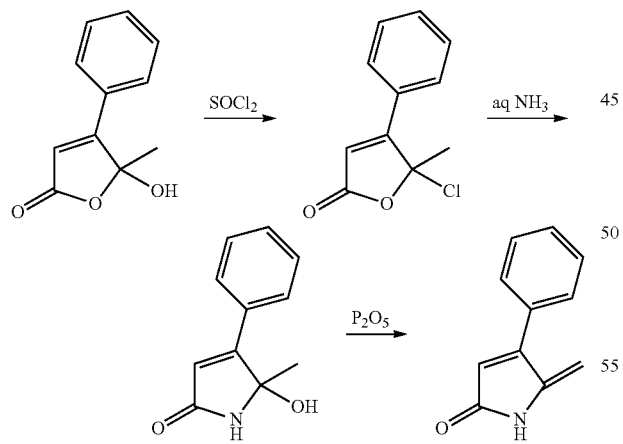

The acid (4.57 g; 0.024 mol) was dissolved in thionyl chloride (20 ml) and heated at reflux for 1.5 hr. Excess thionyl chloride was removed in vacuo; and the residual oil (5.0 g), presumably 5-chloro-5-methyl-4-phenyl-2(5H)furanone, was dissolved in dichloromethane (10 ml) and cooled in an ice-bath. Concentrated aqueous ammonia (15M, 20 ml) was added dropwise over a period of 1 hr, and the reaction mixture left to stir at room temperature over night. The mixture was extracted with ethyl acetate (3×20 ml) and the combined organic phase was dried (sodium sulfate) and flash chromatographed using a plug of silica (EtOAc: $CH_2Cl_2$; 1:1). to yield of 5-hydroxy-5-methyl-4-phenyl)-dihydro-pyrrol-2-one (2.83 g; 62.4%) as a pale brown solid.

A mixture of dihydro-pyrrolone (0.50 g; 2.65 mmol) and $P_2O_5$ (0.50 g; 3.52 mmol) in dichloromethane (20 ml) was stirred at room temperature for 30 min until all of the pyrrolone has dissolved. The mixture was filtered through a celite/silica bed; and washed with $CH_2Cl_2$/EtOAc (1:1). The combined filtrate and washings were evaporated leaving 5-methylene-4-phenyl-2(5H)-pyrrolone as a pale yellow solid (0.34 g; 75%).

Synthesis of 1-methyl-5-methylene-4-phenyl-dihydro-pyrrol-2-one

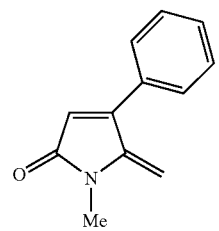

The acid (0.25 g: 1.32 mmol) was heated at reflux with $SOCl_2$ (10 ml) for 3 h. Excess thionyl chloride was removed in vacuo, and the residue dissolved in dichloromethane (20 ml). The residue was cooled in an ice-bath and an aqueous solution of methylamine (10 ml; 24%) was added over a 10 min period. The mixture was left to stir at room temperature overnight. The organic phase was separated, dried over anhydrous sodium sulfate, and the solvent evaporated in vacuo leaving a semi-solid (0.25 g) which was chromatographed using EtOAc as an eluent to yield 1,5-dimethyl-5-hydroxy-4-phenyl-2(5H)pyrolone (0.21 g; 79%) as colourless solid, m.p. 148-152° C.

The alcohol was dissolved in dichloromethane (10 ml) and stirred with $P_2O_5$ (1 g) for 1 h. The mixture was filtered through a celite/silica bed; and washed with $CH_2Cl_2$/EtOAc (1:1). The combined filtrate and washings were evaporated and chromatographed using EtOAc/$CH_2Cl_2$ (1:19) to yield 1-methyl-5-methylene-4-phenyl-2(5H)pyrolone as colourless solid (0.24 g; 49%). $^1$H NMR $\delta$($CDCl_3$): 7.42-7.44 (m, 5H, ArH's); 6.21 (s, 1H, C3-H) and 3.18 (s, 3H, N-Me).

Synthesis of 5-methylene-1,4-diphenyl-dihydro-pyrrol-2-one

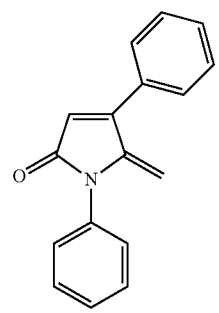 [SMILES: C=C1C(c2ccccc2)=CC(=O)N1c1ccccc1]

5-Hydroxy-5-methyl-4-phenyl-2(5H)furanone (0.20 g; 1.05 mmol) was added to a solution of aniline (2 ml) in toluene (7 ml). The mixture was heated at reflux with stirring for 24 h. After cooling to room temperature, ethyl acetate (20 ml) was added to the mixture and the mixture washed with HCl (2M). The solvent was evaporated in vacuo and chromatographed using $CH_2Cl_2$/EtOAc (19:1) to afford 5-hydroxy-5-methyl-1,4-diphenyl-2(5H)pyrolone (0.12 g; 44%).

The above compound was heated at reflux with a few crystals of p-TSOH in toluene solution for 0.5 h. The mixture was cooled and chromatographed to yield 5-methylene-1,4-diphenyl-dihydro-pyrrol-2-one (0.05 g).

Synthesis of 5-methylene-4-(4'-fluorophenyl)-dihydro-pyrrol-2-one

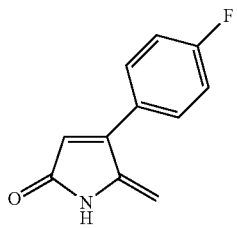

The acid (1.5 g; 6.74 mmol) was dissolved in thionyl chloride (10 ml) and heated at reflux for 3 hr. Excess thionyl chloride was removed in vacuo, and the residual oil (1.8 g) was dissolved in dichloromethane (20 ml) and cooled in an ice-bath. Few crystals of ammonium acetate followed by concentrated aqueous ammonia (15M, 15 ml) was added dropwise over a period of 1 hr, and the reaction mixture left to stir at room temperature over night. The mixture was extracted with ethyl acetate (3×20 ml) and the combined organic phase was dried (sodium sulfate) and evaporated to yield of 5-hydroxy-5-methyl-4(4'-fluoro-phenyl)-dihydro-pyrrol-2-one (0.70 g) as a pale brown solid. $^1$H NMR: δ ($CDCl_3$): 7.78-7.83, 2H, m, Ar H's); 7.1-7.14 (2H, t, Ar H's); 6.67 (s, 1H, —NH); 6.10-6.11 (d, 1H, C3-H); 3.65 (br, 1H, —OH).

The lactam (0.18 g; 0.87 mmol) was dissolved is dry dichloromethane (10 ml) and cooled in an ice bath, whilst $BF_3$.$Et_2$O (0.15 ml) was added drop wise. The mixture was stirred in ice for 1 h, then left to stir at room temperature overnight. The solution was evaporated in vacuo. The residue re-dissolved in $CH_2Cl_2$, washed with water and dried over sodium sulfate. Evaporation of the solvent in vacuo gave 5-methylene-4-(p-fluorophenyl)-2(5H)pyrolone as a pale brown solid (0.15 g; 91%). $^1$H NMR: δ ($CDCl_3$): 7.40-7.46 (2H, m, Ar H's); 7.18 (2H, m, Ar H's); 6.25 (s, 1H, C3-H); 5.06 (d, 1H, C5=$CH_2$) and 5.31 (d, 1H, C5=$CH_2$).

Synthesis of 4-(4'-bromophenyl)-5-methylene-2(5H)pyrrolone

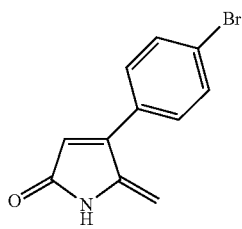

A mixture of 4-(4'-bromophenyl)-5-hydroxy-5-methyl-2(5H)pyrolone (0.17 g; 0.63 mmol) and $P_2O_5$ (0.50 g) in dichloromethane (20 ml) was stirred at room temperature for 45 min until all of the pyrrolone has dissolved. The mixture was diluted with dichloromethane and filtered through a bed of celite/silica. The Celite bed was washed with $CH_2Cl_2$/EtOAc (1:1) and the combined filtrate and washings were evaporated and chromatographed to yield 4-(4'-bromophenyl)-5-methylene-2(5H)pyrolone, (0.06 g; 35%) as a pale yellow solide, m.p. 200° C. (decomp). $^1$H NMR: δ ($CDCl_3$): 8.3 (s, 1H, NH); 7.57-7.6 (d, 2H, Ar H's); 7.29-7.32 (d, 2H; Ar H's); 6.23 (s, 1H, C3-H); 5.15 (d, 1H, C5=$CH_2$) and 4.95 (d, 1H, C5=$CH_2$).

Synthesis of 4-(4'-methoxyphenyl)-5-methylene-2(5H)pyrolone

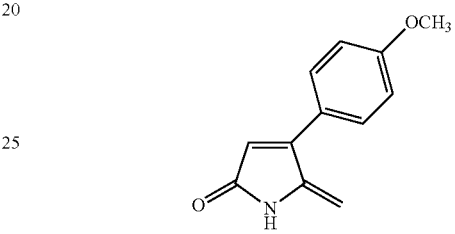

A mixture of 5-hydroxy-5-methyl-4-(4'-methoxyphenyl)-2(5H)pyrolone (0.15 g; 0.68 mmol) and $P_2O_5$ (1 g; 7 mmol)) in dry dichloromethane (10 ml) was stirred at room temperature for 0.5 h, during which time the lactam dissolved. The mixture was diluted with dichloromethane (20 ml), filtered through a pad of celite/silica. The solvent was removed in vacuo and the residue chromatographed to yield 4-(4'-methoxyphenyl)-5-methylene-2(5H)pyrolone (0.61 g; 44%) as a yellow crystalline solid. $^1$H NMR δ ($CDCl_3$) 8.54 (brs; —NH); 7.40 (2H, d, Ar H's); 6.95-6.98 (2H, d, Ar H's); 6.16 (1H, s, C3-H) 5.02 9d, 1H, C5=$CH_2$); 5.15 (d, 1H, C5=$CH_2$) and 3.85 (3H, s, OMe)

Synthesis of 4-benzyl-5-methylene-dihydro-pyrrol-2-one

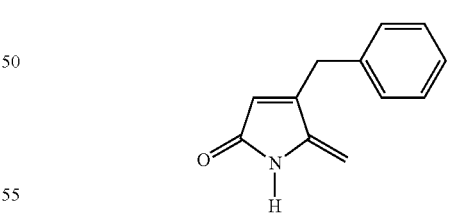

The acid (3.5 g; 0.017 mol) was dissolved in thionyl chloride (20 ml) and heated at reflux for 0.5 hr. Excess thionyl chloride was removed in vacuo, and the residual oil (2.86 g) was dissolved in dichloromethane (20 ml) and cooled in an ice-bath. Aqueous ammonia (15M, 7 ml) was added dropwise over a period of 1 hr, and the reaction mixture left to stir at room temperature over night. The mixture was extracted with ethyl acetate (3×20 ml) and the combined organic phase was dried (sodium sulfate) and evaporated. The resulting brown oil was chromatographed to yield 5-hydroxy-5-methyl-4-benzyl-dihydro-pyrrol-2-one (0.45 g) as a colourless solid.

A mixture of dihydro-pyrrolone (0.45 g) and $P_2O_5$ (0.50 g) in dichloromethane (20 ml) was stirred at room temperature for 30 min until all of the pyrrolone has dissolved. The mixture was filtered through a celite/silica bed; and washed with $CH_2Cl_2$/EtOAc (1:1). The combined filtrate and washings were evaporated leaving 4-benzyl-5-methylene-2(5H)-pyrrolone (0.17 g; 42%) as a pale yellow solid. $^1$H NMR δ(CDCl$_3$): 8.66 (brs; 1H, NH); 7.18-7.31 (5H; m, Ar H's); 5.80 (s, 1H, C3-H); 4.90-4.95 (d, 2H, C5=CH$_2$) and 3.78 (s, 2H, —CH$_2$Ph).

The compounds of Table 1 were also prepared by the general synthetic methodology set out above.

TABLE 1

| Substituents | % Yield/ Melting point degrees Celsius | % Yield/ Melting point degrees Celsius |
|---|---|---|
| R = CH$_3$; R$^1$ = H | 43; 121-123 | 49; oil |
| R = Ph; R$^1$ = H | 98; 249-252 | 75; >230 |
| R = R$^1$ = Ph | 44; 158-160 | 47; 210-212 |
| R = Ph; R$^1$ = CH$_3$ | 79; 148-152 | 49; 112-114 |
| R = 4(F)—Ph; R$^1$ = H | 40; 203-205 | 66; 95-97 |
| R = 4(F)Ph; R1 = Me | 22; 137-140 | 49; 112-114 |
| R = 3(F)Ph; R$^1$ = H | 19; 160 | 65; >230 |
| R = 2(F)Ph ; R = H | 40; 140-143 | 98; >230 |
| R = PhCH$_2$; R$^1$ = H | 66; 175-178 | 42; 110-112 |
| R = 4(Br)Ph; R = H | 93; 255 | 35; >250 |
| R = 4(MeO)Ph; R$^1$ = H | 40; 160-162 | 70; 175 |
| R = 3(MeO)Ph; R$^1$ = H | 17; 167-168 | 48; 170 |
| R = 2(MeO)Ph; R$^1$ = H | 11; 151-152 | 40; >230 |
| R = 3(CF$_3$)Ph; R$^1$ = H | 48; >230 | 36; 190 |
| R = 4(CF$_3$)Ph; R$^1$ = H | 37; 170-173 | 41; 170-173 |

Synthesis of Acrylate and Methacrylate Derivates of Compounds of Formula I and II Preparation of Methacrylate Derivative of 5-hydroxy-5-methyl-4-phenyl-dihydro-pyrrol-2-one 5-Methyl-5-(2'-methylprop-2-enoyloxy)-4-phenyl-dihydropyrrol-2-one and 5-methyl-1-(2'-methylprop-2-enoyl)-(2'-methylprop-2-enoyloxy)-4-phenyl-dihydropyrrol-2-one

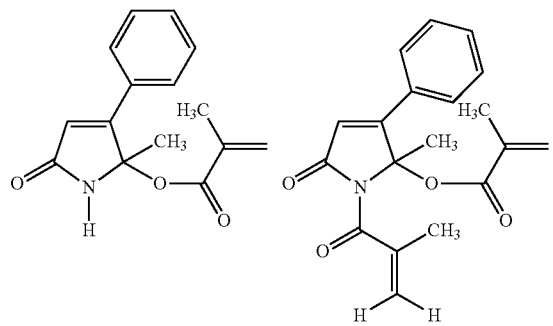

To a suspension of the pseudo acid lactam (020 g; 1.06 mmol) in dry $CH_2Cl_2$ (20 ml), was added triethylamine (1.5 ml; 10.76 mmol) and stirred with cooling in an ice bath. A solution of methacryloyl chloride (1 ml; 9.56 mmol) in dry $CH_2Cl_2$ (3 ml) was added drop wise over min. The mixture was left to stir at this temperature for 2 h. Flash columned with $CH_2Cl_2$/petrol (2:1) giving the methacrylates as a viscous yellow oil (0.25 g; 92%).

5-Methyl-5-(2'-methylprop-2-enoyloxy)-4-phenyl-dihydropyrrol-2-one $^1$H NMR δ (CDCl$_3$): 7.85 (m, 2H, Ar H's); 7.489 (m, 3H, Ar H's); 6.32 (1H, s, C4-H); 5.41 (s, 1H, —NH); 5.36 (s, 1H, —CH$_2$); 5.25 (s, 1H, =CH$_2$); 2.06 (s, 3H, Me) and 2.0 (s, 3H, C5-Me).

5-Methyl-1-(2'-methylprop-2-enoyl)-5-(2'-methyl-prop-2-enoyloxy)-4-phenyl-dihydropyrrol-2-one $^1$H NMR δ (CDCl$_3$): 7.64-7.67 (m, 2H, Ar H's); 7.44-7.47 (m, 3H, Ar H's); 6.48 (1H, s, C4-H); 6.23 (s, 1H, =CH$_2$); 5.66 (d, 1H, =CH$_2$); 5.32 (d, 2H, =CH$_2$); 2.1 (s, 3H, Me) and 2.0 (s, 3H, C5-Me), 1.90 (s, 3H, C5-Me).

Preparation of Acrylate Derivatives of 5-Hydroxy-5-methyl-4-phenyl-dihydro-pyrrol-2-one 5-Methyl-5-(prop-2-enoyloxy)-4-phenyl-dihydropyrrol-2-one and 5-methyl-1-(prop-2-enoyl)-5-(prop-2-enoyloxy)-4-phenyl-dihydropyrrol-2-one

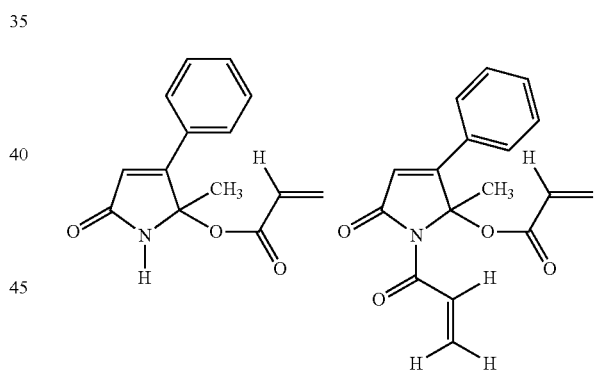

To a solution of the pseudo acid lactam (0.23 g; 1.22 mmol) in dry $CH_2Cl_2$ (10 ml) and dry THF (1 ml), was added triethylamine (1.5 m; 1076 mmol) and few crystals of hydroquinone, while stirring and cooling in an ice bath. A solution of acryloyl chloride (1 ml; 9.56 mmol) in dry $CH_2Cl_2$ (3 ml) was added drop wise over 10 min. The mixture was stirred further for 3 h. The solvent was removed in vacuo at ca 30° C., and the residual semi-solid flash columned with $CH_2Cl_2$ to yield the acrylates as pale yellow solids (0.21 g; 75%).).

5-Methyl-5-(prop-2-enoyloxy)-4-phenyl-dihydropyrrol-2-one $^1$H NMR δ (CDCl$_3$): 7.88 (m, 2H, Ar H's); 7.48 (m, 3H, Ar H's); 6.62 (d, 1H, =CH$_2$); 6.34 (1H, s, C4-H); 5.95 (dd, 1H, =CH); 5.30 (s, 1H, =CH$_2$) 1.92 (s, 3H, C5-Me).

5-Methyl-1-(prop-2-enoyl)-5-(prop-2-enoyloxy)-4-phenyl-dihydropyrrol-2-one $^1$H NMR δ (CDCl$_3$): 7.65 (m, 2H, Ar H's); 7.43-7.60 (m, 4H, Ar H+CH$_2$); 6.46-6.53 (m, 3H, =CH$_2$ and C3-H); 6.13-6.16 (dd, 1H, —CH—); 5.8-6.0 (m, 2H, =CH$_2$) and 2.1 (s, 3H, C5-Me).

Preparation of Methacrylate Derivatives of 5-methylene-4-phenyl-dihydro-pyrrol-2-one

Synthesis of 5-Methylene-1-(2'-methylprop-2-enoyl)-4-phenyl-dihydropyrrol-2-one

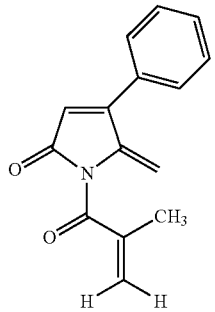 [SMILES: C=C(C)C(=O)N1C(=C)C(c2ccccc2)=CC1=O]

Trifluoroacetic acid (1.5 ml) was added to a solution of 5-methyl-1-(2'-methylprop-2-enoyl)-5-(2'-methylprop-2-enoyloxy)-4-phenyl-dihydropyrrol-2-one (1.45 g, 4.46 mmol) in dichloromethane. The mixture was stirred at room temperature for 2 h and washed successively with saturated sodium bicarbonate solution and water. The dichloromethane layer was separated, dried over sodium sulfate and chromatographed on a silica column using dichloromethane as an eluent to yield 5-methylene-1-(2'-methylprop-2-enoyl)-4-phenyl-dihydropyrrol-2-one (0.64 g, 60%) as colourless granules.

$^1$H NMR δ (CDCl$_3$): 7.48 (m, 5H, Ar H's); 6.23 (s, 1H, =CH$_2$); 6.14 (1H, s, C4-H); 5.55 (bs, 1H, —CH$_2$); 5.36 (s, 1H, =CH$_2$).

Preparation of Acrylate Derivatives of 5-methylene-4-phenyl-dihydro-pyrrol-2-one

Synthesis of 5-Methylene-1-(prop-2-enoyl)-4-phenyl-dihydropyrrol-2-one

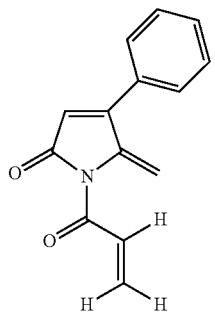 [SMILES: C=CC(=O)N1C(=C)C(c2ccccc2)=CC1=O]

Trifluoroacetic acid (1.0 ml) was added to a solution of 5-methyl-1-(prop-2-enoyl)-5-(prop-2-enoyloxy)-4-phenyl-dihydropyrrol-2-one (0.44 g, 1.48 mmol) in dichloromethane (9 ml). The mixture was stirred at room temperature for 2 h and washed successively with saturated sodium bicarbonate solution and water. The dichloromethane layer was separated, dried over sodium sulfate and chromatographed on a silica column using dichloromethane as an eluent to yield 5-methylene-1-(prop-2-enoyl)-4-phenyl-dihydropyrrol-2-one (0.18 g, 51%) as colourless granules.

$^1$H NMR δ (CDCl$_3$): 7.46 (m, 5H, Ar H's); 6.70 (s, 1H, =CH$_2$); 6.59 (d, 1H, =CH$_2$); 6.15 (1H, s, C4-H); 5.93 (d, 1H, =CH$_2$); 5.41 (s, 1H, =CH$_2$).

In a similar manner, the acrylate derivatives of other 4-phenyl-5-methylene-dihydropyrrol-2-ones were prepared.

2. Antibacterial Assays

A number of assays were carried out on the compounds of the present invention. The experimental methodology of these assays is set out below.

2(a) N-acylated Homoserine Lactone (AHL) Quorum Sensing Assay

The present applicant has demonstrated that certain furanones and furanone analogues can inhibit AHL-mediated quorum sensing in bacteria. Compounds of the present invention were compared to compounds of the prior art in order using an AHL-quorum sensing assay which utilises a reporter strain that expresses Green Fluorescent Protein (GFP) in the presence of AHL signals. The assay is performed by measuring GFP output in the presence of the compound to be measured and comparing the output to a control. By using multiple samples at varying concentrations of compound and AHL, an inhibition index of compound activity can be generated. The inhibition index used in the present example is the relative amount of compound required to reduce GFP expression to 40% of the control. The inhibition index is termed AIC40. Lower values of AIC40 represent better inhibitors of the AHL quorum sensing system.

The reporter strain of bacterium used in this assay is *E. coli* into which the *V. fischeri* luxRI system has been engineered. A gfp gene is fused to the QS controlled luxI promoter as is described in (Andersen et al., 2001, and Andersen et al, 1998).

Measurement of AIC40 (ID40 at 3 nM OHHL)

Determination of the activity of compounds using the *E. coli* based luxRI construct was performed as follows.

Inhibition Kinetics

In a 15 mL plastic tube, mix 3 mL of o.n. culture of the lux reporter strain with 12 mL fresh medium, incubate at 37° C. Label six tubes, 10, 20, two 50 and two 100. To each of the tubes, add OHHL (3-oxohexanoyl homoserine lactone) to a final concentration of 10, 20, 50, or 100 nM respectively in the AB medium (add enough medium to distribute across the appropriate number of wells). To the first row of the microplate (row A), add 200 ul of the OHHL/AB mixture. To the remaining rows (B-H) add 100 ul of the OHHL/AB mixture. To the first row (A) add compounds to be tested to the 200 ul mixture of OHHL/AB. Make a dilution series in the first 7 rows by transferring 100 μL from wells in row 1 to wells in row 2 and so on. Discard the remaining 100 μL from row 7. Add 100 μL diluted lux monitor to each well. Incubate the plate 2 hours at 37° C. and measure green fluorescence using the "Victor" plate reader.

Data Treatment

Calculate $ID_{40}$ for each column. To do this, calculate the relative activity in each well. Each column is calculated separately, the well that does not contain furanone is set to 100% activity (the wells in row 8). Make a plot for each concentration of OHHL vs. the range of compound concentrations used. Calculate the amount of compound needed to lower the relative activity to 40%, this is termed inhibiting dose 40%, $ID_{40}$. For each compound an inhibition index, $AIC_{40}$, is found as follows: plot $ID_{40}$ against its respective AHL concentration; $AIC_{40}$ is the slope of the best straight line through the plotted points and origin.

2(b) LasR Assay

Compounds of the present invention were also assayed using a LasR assay. The LasR assay provides a measurement of quorum sensing inhibition activity. The higher the percentage inhibition. The more effective the compound. In the LasR assay, an unstable gfp has been fused to the elastase promoter, so that the amount of Gfp is regulated by the QS system. The plasmid is put into *Pseudomonas aeruginosa* which makes its own AHL signals. The assay is performed by adding the compounds to be tested to the system at the beginning of the experiment, at different concentrations. Gfp expression is measured at different times during growth, ending at the 24 h time point. The percentage fluorescence was determined at the time point when the fluorescence reached its maximum in the control, usually around 11-12 h after inoculation.

Example 2(c) *S. epidermidis* Growth

The growth inhibition of *Staphylococcus epidermidis* by the compounds of the present invention was determined by growing *S. epidermidis* in 96 well microtitre plates in Trypticase Soy Broth plus 0.5% glucose in a Wallac Victor2 microplate reader. Each compound was added to the wells at different concentrations and a no-compound control and a set of blank wells were also used. The OD600 was measured hourly. Growth curves were generated and the growth of the cells in the presence of the compound is compared to the controls to determine the concentration of compound that significantly alters growth rate or final growth yield.

Example 2(d)

Inhibition of Biofilm Formation

Biofilm formation in petri dishes was measured using the following protocol as a compromise between flow cells and microtitire plate based assays. The method increases the number of replicates (relative to flow cells) that can be tested while still generating a biofilm that has typical structures, such as microcolonies, which are important as differentiated structures within the biofilm. The method consists of placing a surface, such as a glass slide (for unattached compounds) or a modified plastic coupon (for covalently attached compounds) on the bottom of a sterile petri dish and adding growth medium. The bacteria are inoculated into the dish and allowed to incubate at the appropriate temperature at 50 rpm. The medium is replaced at 24 h and allowed to incubate a further 24 h, after which time, the slides are removed and rinsed to remove loosely attached cells. For monitoring biofilm formation on glass slides, the cells are either stained with a suitable fluorescent stain and are visualised using the confocal microscope and the biofilm (as % surface coverage) is quantified, or the biofilm is stained with crystal violet, washed thoroughly to remove excess stain, and subsequently destained and the absorbance at 540 mm is measured to determine the amount of biofilm, as a function of crystal violet staining.

Compound Measurements

Assay results for a number of compounds according to the present invention using the assays set out in Examples 2(a)-2(d) are set out in Tables 2 and 3.

TABLE 2

| Compd | $AIC_{40}$ | LasR (conc) | *S. epidermidis* growth | *P. aeruginosa* biofilm | *S. epidermidis* biofilm | *E. coli* biofilm |
|---|---|---|---|---|---|---|
| (phenyl pyrrolone structure) | 1.1 | 80% (50 ug/ml) | 5 ug/ml | 88% (10 ug/ml) | NE | 95% (5 ug/ml) |
| (4-fluorophenyl pyrrolone structure) | 4.61 | 61% (50 ug/ml) | 20 ug/ml | 78% (12.5 ug/ml) | 40% (10 ug/ml) | |

TABLE 2-continued
| Compd | AIC40 | LasR (conc) | S. epidermidis growth | P. aeruginosa biofilm | S. epidermidis biofilm | E. coli biofilm |
|---|---|---|---|---|---|---|
| 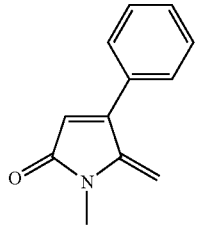 | 52.76 | 40% (50 ug/ml) | | | | |
| 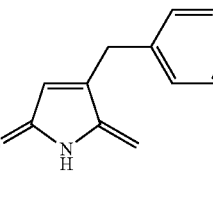 | 69.45 | 61% (50 ug/ml) | | NE | | |
| 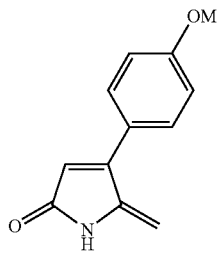 | 5.4 | 36% (25 ug/ml) | | 76% (25 ug/ml) | | |
| 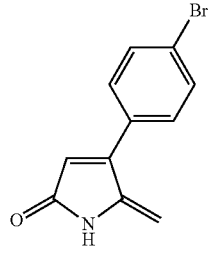 | 0.49 | 45% (50 ug/ml) | 1 ug/ml | 32% (1 ug/ml) | 41% (0.32 ug/ml) | 93% (1.5 ug/ml) |
| 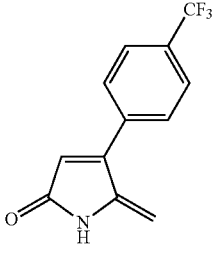 [SMILES: C=C1NC(=O)C=C1c1ccc(C(F)(F)F)cc1] | 1 | 54% (25 ug/ml) | 1 ug/ml | | NE | |
| 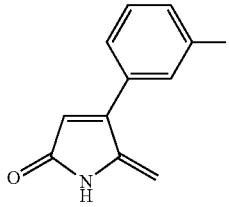 | 4.6 | 40% (25 ug/ml) | 0.5 ug/ml | | NE | |

TABLE 2-continued
| Compd | AIC40 | LasR (conc) | S. epidermidis growth | P. aeruginosa biofilm | S. epidermidis biofilm | E. coli biofilm |
|---|---|---|---|---|---|---|
| 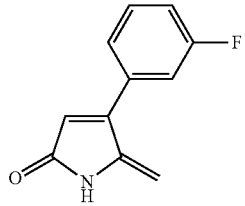 309 | 1.3 | 70% (25 ug/ml) | 0.5 ug/ml | NE | NE | |
| 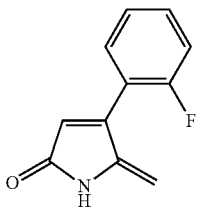 | 1.7 | 60% (25 ug/ml) | 20 ug/ml | NE | 60% (0.3 ug/ml) | |
TABLE 3
| Compd | AIC40 | LasR (conc) | S. epidermidis growth | P. aeruginosa biofilm | S. epidermidis biofilm | E. coli biofilm |
|---|---|---|---|---|---|---|
| 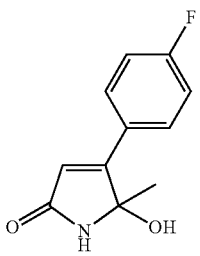 | NE | 28% (100 ug/ml) | 100 ug/ml | NE | NE | |
| 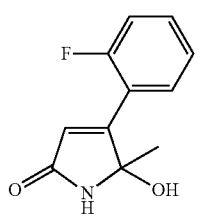 | 9.9 | 40% (100 ug/ml) | >100 ug/ml | 12% (20 ug/ml) | 17% (50 ug/ml) | |
| 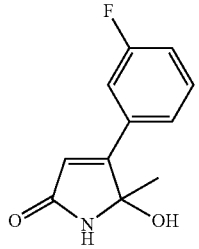 | NE | NE | >100 ug/ml | | | |

TABLE 3-continued

| Compd | AIC40 | LasR (conc) | S. epidermidis growth | P. aeruginosa biofilm | S. epidermidis biofilm | E. coli biofilm |
|---|---|---|---|---|---|---|
| 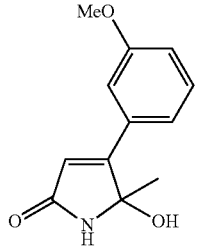 [SMILES: COc1cccc(C2=CC(=O)NC2(C)O)c1] | NE | NE | >50 ug/ml | | | |
| 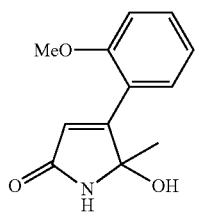 [SMILES: COc1ccccc1C1=CC(=O)NC1(C)O] | NE | 41% (100 ug/ml) | >50 ug/ml | | | |
| 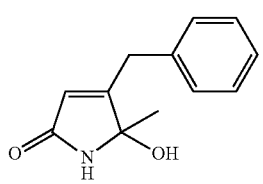 | NE | NE | >100 ug/ml | | | |

NE, no effect

All percentages are percent reduction of control at non-growth inhibitory concentrations Numbers in parentheses indicate concentration used

Example 2(e)

Pulmonary Model of Infection: Mice Challenged with Bacteria/Seaweed Alginate through the Trachea This model is reminiscent of the situation in CF patients or patients with a dysfunctional muccociliary escalator.

Experiment:

The treatment dosage of 5-methylene-4-phenyl-dihydro-pyrrol-2-one (C219) was 12 μg/g body weight, given as injections twice a day.

Mice were challenged with *Pseudomonas aeruginosa* PAO1 (wt) $5.2 \times 10^6$ CFU/lung ($1.3 \times 10^8$ CFU/ml). Each group holds 10 mice, the treatments with C219 and Vehicle lasted for three days. The mortality was 10% in C219 and 30% in Vehicle groups. At day 5, the surviving mice were sacrificed. LIMP (the fraction of the total lung area of the lung that shows inflammation) and bacterial content in the lungs were determined.

Result:

The treatment of C219 significantly reduced the lung bacterial load compared to Vehicle groups on day 5 (p=0.0008) (FIG. 1).

C219 treatment (two injections per day each 12 μg/g body weight given for three days) significantly reduced the severity (LIMP) of P aeruginosa (PA) lung infection in mice to placebo (vehicle=control). Therefore, the compounds seem to exert a positive effect on inflammation.

3. Comparative Studies

The antibacterial activity and cytotoxicity of compounds according to the present invention were compared to compounds similar to those exemplified in WO 2004/016588.

3(a) N-acylated Homoserine Lactone (AHL) Quorum Sensing Assay

The methodology for this assay is set out in 2(a) above.

Compounds 219, 257, 294, 295 according to the present invention and compounds 198 and 205 which are similar to the compounds exemplified in WO 2004/016588 were assayed and the results are shown in Table 4. As can be seen compounds 219, 257, 294 and 295 have significantly better AIC40 values than compounds 198 and 205.

TABLE 4

Comparative results of N-acylated homoserine lactone (AHL) quorum sensing assay
Change to correspond to initial data

| Compound | AIC40 (ID40 at 3 nM OHHL) |
|---|---|
| 219 (4-phenyl pyrrolinone, exocyclic =CH-H, NH) | 1.1 (16.2) |
| 257 (4-(4-fluorophenyl) pyrrolinone, exocyclic =CH-H, NH) | 4.61 (17.61) |
| 273 (4-phenyl pyrrolinone, N-Me, exocyclic =CH2) | 52.76 (163.26) |
| 276 (4-benzyl pyrrolinone, exocyclic =CH2, NH) | 69.45 (239.79) |
| 294 (4-(4-methoxyphenyl) pyrrolinone, exocyclic =CH-H, NH) | 5.4 (61 nM) |
| 295 (4-(4-bromophenyl) pyrrolinone, exocyclic =CH2, NH) | 0.49 (21 nM) |
| 198 (3-bromo-4-... N-benzyl, exocyclic =CHBr) | 27 |
| 205 (3-bromo, 1-hydroxybutyl, N-phenyl, exocyclic =CHBr) | 99 |

3(b) Cytotoxicity Study

Compounds were tested for cytotoxic activity using the following assay:

Murine L929 cells are established at low density and, during the testing period, grow to confluency in plastic petri dishes. 24 hours after the dishes are inoculated, the medium on the test dishes is aspirated and replaced with a medium containing the compound to be tested. The cell monolayer is then cultured for a further 48 hour period. At the end of the test period, cells are harvested from the dishes and their numbers assessed and compared with unperturbed cultures. Differences in cell numbers are expressed as a percentage inhibition in comparison to non-challenged cultures. An inhibition of 30% is considered clear indication of cytotoxic potential in the test compound.

Cell Line:

Earle's L Cells—NCTC Clone 929 (Murine) grown in MEM/NA supplemented with 10% FBS The compounds tested were 219, a compound according to the present invention, and compounds 226 and 223 which are dibromo-substituted lactams which have the same bromination pattern as compounds exemplified in WO 2004/016588. The results of the assay are set out in Table 5.

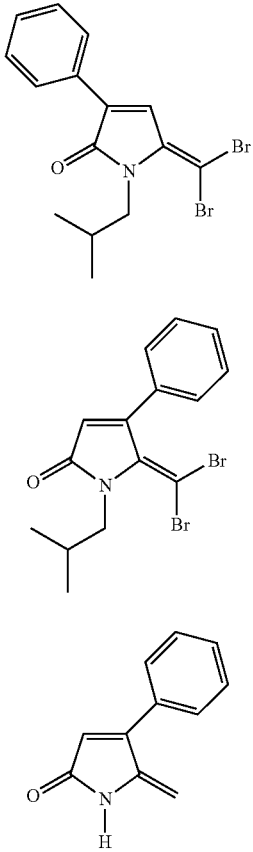

TABLE 5

| Treatment | Mean | Std Dev | % Inhibition |
|---|---|---|---|
| Null (NaCl) | 4.91E+05 | 1.66E+04 | 0.0 |
| 4% Ethanol | 3.40E+05 | 1.85E+04 | 30.7 |
| 5% Ethanol | 3.09E+05 | 1.08E+04 | 36.9 |
| 7.5% Ethanol | 7.63E+04 | 2.36E+04 | 84.5 |
| 219 (40 µg/ml) | 4.74E+05 | 2.09E+04 | 3.4 |
| 219 (20 µg/ml) | 4.95E+05 | 3.04E+04 | −1.0 |
| 219 (10 µg/ml) | 5.41E+05 | 7.34E+03 | −10.3 |
| 226 (40 µg/ml) | 1.67E+05 | 5.39E+03 | 61.6 |
| 226 (20 µg/ml) | 2.42E+05 | 1.42E+04 | 44.4 |
| 226 (10 µg/ml) | 2.14E+05 | 1.52E+04 | 50.9 |
| 226 (5 µg/ml) | 3.41E+05 | 2.50E+04 | 21.8 |
| 223 (40 µg/ml) | 2.07E+05 | 6.80E+04 | 52.4 |
| 223 (20 µg/ml) | 2.94E+05 | 2.06E+04 | 32.5 |
| 223 (10 µg/ml) | 3.31E+05 | 2.33E+04 | 24.1 |
| DMSO | 4.97E+05 | 1.09E+04 | −1.3 |

NB E+05 is equivalent to ×10$^5$

Compound 219, a compound according to the present invention, displays surprisingly little or no cytotoxicity when compared with the structurally related compounds 226 and 223 which are similar to those exemplified in WO 2004/016588.

4. Attachment of Compounds to Surfaces

4(a) Copolymerisation of 219-methacrylate with HEMA Monomers

HEMA (hydroxyethylmethacrylate) contact lenses were made using a HEMA formulation and 219-methacrylate. The copolymer solution was poured into a two-part contact lens mould and cured under 365 nm blue/black lamps for 30 minutes followed by an additional 30 minutes in an oven at 115° C. to complete the process. Upon cooling, the cured lenses were removed from the moulds and hydrated in PBS, then rinsed and stored in PBS.

4(b) Surface Attachment of Acrylates and Methacrylates of Compounds of Formula I and II Amino and thiol functionalised surfaces can be reacted with an acrylate derivative of lactam in a Michael addition fashion. This strategy is quite versatile and would result in covalent attachment of the lactam moiety in a single step.
General Attachment Procedure Silicone rubber sheets or catheters are functionalized with amino groups by techniques known to those skilled in the art. These techniques include activation of the surface by exposure to plasma in a plasma chamber and then exposing the surface to heptyamine vapour and direct reaction of the surface with aminopropyltriethoxysilane. Other suitable techniques for functionalisation of silicone surfaces are also known to those skilled in the art. The sheets or catheters are soaked overnight with agitation in glass vials containing alcoholic or aqueous alcoholic solution of a compound of Formula I or II bearing an acrylate or methacrylate substituent (for example 1 mg/mL in 50% ethylene glycol, 10% ethanol, 40% Milli Q water). The coated sheets or catheters are removed from the reaction mixture with tweezers and washed (agitated for 10 minutes) three times in vials containing 10 ml of fresh alcohol solution or mixture of 50% ethylene glycol, 10% ethanol, 40% Milli Q water. The silicone sheets or catheters are then washed three times with Milli Q water and once with PBS and stored in PBS.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

ANDERSEN, J. B., HEYDORN, A., HENTZER, M., EBERL, L., GEISENBERGER, O., CHRISTENSEN, B.,

BAK, MOLIN, S. & GIVSKOV, M. (2001) Gfp-based n-acyl homoserine lactone sensor systems for detection of bacterial communication. *Appl. Environ. Microbiol.*, 67, 575-585.

ANDERSEN, J. B., STERNBERG, C., POULSEN, L. K., BJORN, S. P., GIVSKOV, M. & MOLIN, S. (1998) New unstable variants of green fluorescent protein for studies of transient gene expression in bacteria. *Appl. Environ. Microbiol*, 64, 2240-2246.

The invention claimed is:

1. A compound of formula I:

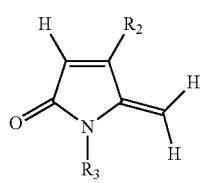

wherein:
$R_2$ is selected from the group consisting of heterocyclyl, heteroaryl, aryl and arylalkyl;
$R_3$ is selected from the group consisting of hydrogen, hydroxy, alkyl, cycloalkyl, alkoxy, oxoalkyl, alkenyl, heterocyclyl, heteroaryl, cycloalkyl, aryl, arylalkyl, and —C(O)CR$_6$=CH$_2$;
$R_6$ is selected from the group consisting of hydrogen or methyl.

2. A compound selected from the group consisting of
5-methylene-4-phenyl-dihydro-pyrrol-2-one;
1-methyl-5-methylene-4-phenyl-dihydro-pyrrol-2-one;
5-methylene-1,4-diphenyl-dihydro-pyrrol-2-one;
4-(4'-bromophenyl)-5-methylene-2-dihydro-pyrrol-2-one;
4-benzyl-5-methylene-dihydro-pyrrol-2-one;
4-(4'-methoxyphenyl)-5-methylene-dihydro-pyrrol-2-one;
5-methylene-4-(4'-fluorophenyl)-dihydro-pyrrol-2-one;
5-methylene-4-(4'-trifluoromethylphenyl)-dihydro-pyrrol-2-one;
5-methylene-4-(3'-trifluoromethylphenyl)-dihydro-pyrrol-2-one;
5-methylene-4-(2'-fluorophenyl)-dihydro-pyrrol-2-one; and
5-methylene-4-(3'-fluorophenyl)-dihydro-pyrrol-2-one.

3. A method of treating a microbial infection caused by an organism selected from the group consisting of *S. epidermis, P. aeruginosa* and *E. coli* in a subject, the method comprising administering a compound according to claim 1 to the subject.

4. A method of treating a microbial infection caused by an organism selected from the group consisting of *S. epidermis, P. aeruginosa* and *E. coli* in a subject, the method comprising administering a compound according to claim 2 to the subject.

5. A method according to claim 3 wherein the infection is a bacterial infection.

6. A method according to claim 3 wherein the infection is characterised by biofilm formation.

7. A method of inhibiting microbial contamination of a surface by an organism selected from the group consisting of *S. epidermis, P. aeruginosa* and *E. coli*, the method comprising administering a compound according to claim 1 to the surface.

8. A formulation comprising a compound according to claim 1 and a carrier.

9. A formulation comprising a compound according to claim 2 and a carrier.

10. A compound according to claim 1 wherein $R_3$ is —C(O)CR$_6$=CH$_2$.

11. A compound according to claim 10 when used to form an oligomer or polymer.

12. A compound according to claim 11 wherein the oligomer or polymer is formed by polymerisation of a terminal vinyl group of the compound.

13. A polymer or oligomer formed by oligomerising or polymerising a compound accordingly to claim 10 directly or with one or more other monomers.

14. A compound according to claim 10 wherein a terminal vinyl group of the compound is reacted with a functional group.

15. A compound according to claim 10 when attached to a surface.

16. A compound according to claim 15 wherein the compound is attached to the surface by reaction of a terminal vinyl group of the compound with a functional group.

17. A surface comprising one or more compounds according to claim 10 attached to the surface.

18. A surface comprising the polymer or oligomer according to claim 13 attached to the surface.

19. A compound of formula II:

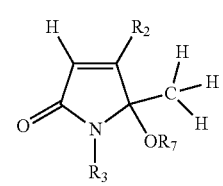

wherein
$R_3$ is selected from the group consisting of hydrogen, hydroxy, alkyl, cycloalkyl, alkoxy, oxoalkyl, alkenyl, heterocyclyl, heteroaryl, aryl, arylalkyl, and —C(O)CR$_6$=CH$_2$;
$R_6$ is selected from the group consisting of hydrogen and methyl;
$R_7$ is —C(O)CR$_6$=CH$_2$;
and $R_2$ is selected from the group consisting of heterocyclyl, heteroaryl, aryl and arylalkyl.

20. A method of treating a microbial infection caused by an organism selected from the grup consisting of *S. epidermis, P. aeruginosa* and *E. coli* in a subject, the method comprising administering a compound according to claim 19 to the subject.

21. A method according to claim 20 wherein the infection is a bacterial infection.

22. A method according to claim 20 wherein the infection is characterised by biofilm formation.

23. A method of inhibiting microbial contamination of a surface by an organism selected from the group consisting of *S. epidermis. P. aeruginosa* and *E. coli*, the method comprising administering a compound according to claim 19 to the surface.

24. A formulation comprising a compound according to claim 19 and a carrier.

25. A compound according to claim 19 wherein at least one of $R_3$ and $R_7$ is selected from —C(O)CR$_6$=CH$_2$.

26. A compound according to claim 25 wherein each of $R_3$ and $R_7$ is selected from $—C(O)CR_6=CH_2$.

27. A compound according to claim 25 when used to form an oligomer or polymer.

28. A compound according to claim 27 wherein the oligomer or polymer is formed by polymerisation of a terminal vinyl group of the compound.

29. A polymer or oligomer formed by oligomerising or polymerising a compound accordingly to claim 25 directly or with one or more other monomers.

30. A compound according to claim 25 wherein a terminal vinyl group of the compound is reacted with a functional group.

31. A compound according to claim 25 when attached to a surface.

32. A compound according to claim 30 wherein the compound is attached to the surface by reaction of a terminal vinyl group of the compound with a functional group.

33. A surface comprising one or more compounds according to claim 25 attached to the surface.

34. A surface comprising the polymer or oligomer according to claim 29 attached to the surface.

* * * * *